United States Patent [19]

Reichenberger et al.

[11] Patent Number: 4,962,752

[45] Date of Patent: Oct. 16, 1990

[54] COUPLING MEMBER FOR A SHOCK WAVE THERAPY DEVICE

[75] Inventors: Helmut Reichenberger, Eckental; Georg Naser, Zindorf; Helmut Jahn, Erlangen Buckenhof, all of Fed. Rep. of Germany

[73] Assignee: Siemens Aktiengesellschaft, Berlin and Munich, Fed. Rep. of Germany

[21] Appl. No.: 279,106

[22] Filed: Dec. 2, 1988

Related U.S. Application Data

[62] Division of Ser. No. 13,504, Feb. 9, 1987, Pat. No. 4,813,402.

[30] Foreign Application Priority Data

Feb. 19, 1986 [DE] Fed. Rep. of Germany ....... 3608277
Aug. 18, 1986 [DE] Fed. Rep. of Germany ....... 3627943

[51] Int. Cl.$^5$ .................................................. A61B 17/22
[52] U.S. Cl. ........................................ 128/24 A; 73/644
[58] Field of Search ............ 128/328 R, 328 S, 24 A, 128/660.01, 0.03, 0.08–0.09, 660.1, 662.03; 606/127, 128; 73/644

[56] References Cited

U.S. PATENT DOCUMENTS

| | | | |
|---|---|---|---|
| 3,973,235 | 8/1976 | van der Burgt | 128/660.01 |
| 4,277,367 | 7/1981 | Madsen et al. | |
| 4,311,147 | 1/1982 | Hausler | 128/328 S |
| 4,459,854 | 7/1984 | Richardson et al. | |
| 4,526,168 | 7/1985 | Hassler et al. | 128/328 S |
| 4,539,989 | 9/1985 | Forssmann et al. | 128/328 S |
| 4,542,745 | 9/1985 | Oakley et al. | 128/660.01 |
| 4,579,123 | 4/1986 | Chen et al. | 73/644 X |
| 4,630,607 | 12/1986 | Duinker et al. | 128/328 |
| 4,655,220 | 4/1987 | Hahn et al. | 128/328 |
| 4,674,505 | 6/1987 | Pauli et al. | |
| 4,674,514 | 6/1987 | Abbott et al. | |
| 4,696,299 | 9/1987 | Shene et al. | 128/328 S |
| 4,734,611 | 3/1988 | Granz | |

FOREIGN PATENT DOCUMENTS

2003701 3/1979 United Kingdom .
2102657 2/1983 United Kingdom .
2140693 12/1984 United Kingdom .

Primary Examiner—Ruth S. Smith
Attorney, Agent, or Firm—Hill, Van Santen, Steadman & Simpson

[57] ABSTRACT

A coupling member for transmission of shock waves from a shock wave device to a patient to be treated is composed of an elastic, shape-stable material having a moist outside surface, and is preferably formed of a hydro-gel, such as a polyacrylamide gel. The material is provided with an insert which contributes to its good stability and also enables manipulation of the member. The coupling member can also include, with or without the insert, a shock wave sensor which is embedded in the material and enables checking the power and the position or center of the shock wave source relative to a predetermined point.

11 Claims, 4 Drawing Sheets

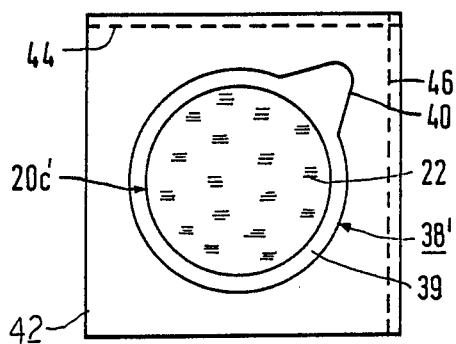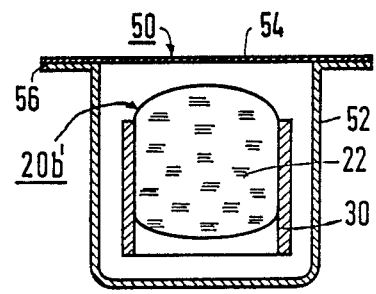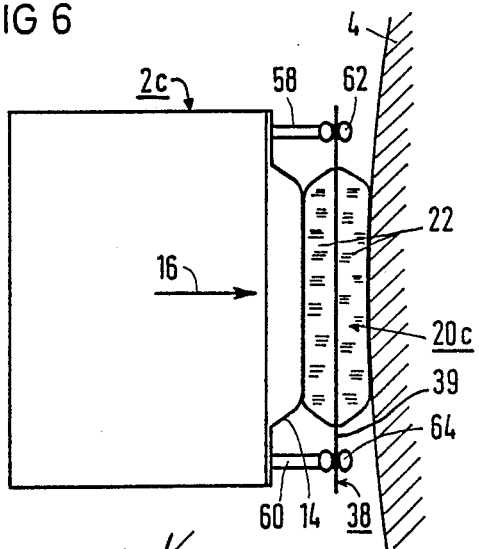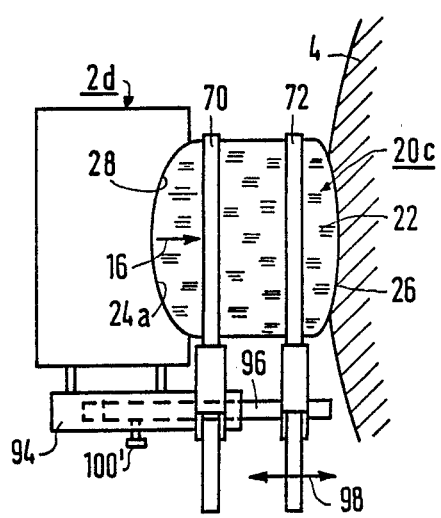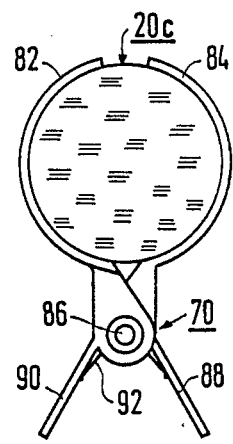

COUPLING MEMBER FOR A SHOCK WAVE THERAPY DEVICE

This is a division of application Ser. No. 013,504, filed Feb. 9, 1987, now U.S. Pat. No. 4,813,402.

BACKGROUND OF THE INVENTION

The present invention is directed to a coupling member for a transmission of shock waves from a shock wave source onto a patient to be treated.

In the field of medical diagnostic apparatus, which work with ultrasound, it is known to couple the ultrasound applicator to the patient to be examined by means of a coupling paste. Such a paste has a disadvantage that air inclusions can occur at the boundary surface between the applicator and the patient when the applicator is removed and reapplied. These air inclusions lead to disturbances in the ultrasound image. It is also known in this field to employ preliminary paths for the diagnostic examination of patients and these paths have their speed of sound adapted to that of the body tissue. These preliminary paths are generally formed as containers, which include bags, sacks or the like, and are filled with a liquid such as, for example, water. The container is usually coupled with a coupling paste to the ultrasound oscillation exciter and to the patient. In this way, disturbing reflections at the boundary surface of the ultrasound applicator and also at the boundary surface of the examination, subject can be avoided.

The invention is not related to an ultrasound diagnostic installation, but rather to a shock wave therapy means, namely a means for disintegrating of a concretions in the body of a life form. Such a means for disintegration or disaggretation is disclosed, for example, in German OS No. 33 28 039 and in copending U.S. patent application Ser. No. 634,021, filed July 24, 1984, which application issued as U.S. Pat. No. 4,674,505 and claims priority from German Patent Application No. 33 28 051. In this disintegration device as well, a coupling paste has heretofore been utilized for coupling and thus for transmitting shock waves on the path from the shock wave source to the patient to be treated. Even when a rubber-elastic member, for example as disclosed in German OS No. 33 12 014, a liquid-filled pillow, for example as disclosed in U.S. Pat. No. 4,539,989 which claimed priority from German Application No. 31 46 626, or a liquid-filled accordion bellows, for example as disclosed in German OS No. 33 19 871, was employed in such a disintegration device on this path, a free-flowing coupling paste, nevertheless, had to be employed for coupling these elastic component parts, at least on the side of the patient. The use of such a coupling paste, however, requires a thorough preparation of the patient before the actual therapeutic treatment and also requires a careful cleaning of the patient, and under given conditions of the shock wave apparatus as well after its use.

It would therefore be desirable if the coupling paste could be replaced with a coupling member which, first, guarantees an acoustical reliable coupling of the shock waves without gas inclusion at the boundary surface, which makes involved cleaning after the treatment superfluous and which is simple to handle in terms of manipulation.

A coupling member in the field of ultrasound wherein the first two demands are met is disclosed in U.S. Pat. No. 4,459,854, which claims priority from an application resulting in the U.K. Patent Application GB No. 2,102,657. The problem of manipulating of the gel compound is not discussed in further detail in this reference.

SUMMARY OF THE INVENTION

Thus, it is an object of the present invention to provide a coupling member for a transmission of shock waves on the path from a shock wave source to a patient which is to be treated, which coupling member guarantees a reliable, reproduceable coupling, and which coupling is easy to manipulate and guarantees clean work.

These objects are obtained in the invention in a coupling member which is formed of an elastic, shape-stable material having moist outside surfaces, and is provided with an insert which insert projects beyond the plastic shape-stable material and forms means at the projecting part for grasping the member.

The elastic, shape-stable material can preferably be a hydro-gel. Hydro-gels are materials which contain water as a matrix. Such a hydro-gel would, of course, also include gelatins. However, a polyacrylamide gel is of particular advantage for use in the transmission of shock waves. Such a material is extremely shape-stable, for example, easy to manipulate and can be easily brought into a definite shape. During use, first it is easily adapted to the contour of the patient's body, and secondly, to the exit face of the shock wave generator.

The polyacrylamide gel for the coupling member is preferably synthesized from:
(a) an Acrylamide (as a monomer);
(b) N, N'-methylene-bis-acrylamide (as a cross-linker);
(c) ammoniumpersulfate (as a catalyst);
(d) N, N, N', N'-tetramethylethylene-diamine (as a starter); and
(e) water (as a diluent).

The preparation is as thin-bodied as water. Arbitrary shapes of the coupling member can be cast with this material. After polymerization has been carried out, a transparent, soft elastic and relatively rip-proof gel member having low attenuations for the shock waves and having an impedance adapted to the human tissue is present. Hard-elastic through viscous gels can be manufactured by modifying the monomer-to-water ratio.

Polyacrylamide gels are, for example, co-polymerisates of acrylamide and methylene-bis-acrylamide, whose pore width is dependent on the graduation between the monomeric and the cross-linked partners. The polyacrylamide gels and receptors for their manufacture are known per se. In the prior art, they are suitable as molecular sieves for separating, desalinizing and concentrating substances having high molecular weight. For example, they are also utilized in gel chromatography; and their manufacture can be undertaken with commercially available raw materials in accordance with known formulas, such as disclosed by H. Determann, *Gelchromatographie,* Springer-Verlag, Berlin, Heidelberg, N.Y., pages 19–21 and page 31. Their properties have been investigated in detail as set forth in *Spektrum der Wissenschaft,* March 1981, pages 79–93. Polyacrylamide gels are also employed for electrophoreus and suitable reagents are offered for this purpose (see for example Desaga Katalog, Desaga Company, Heidelberg, pages 49 and 54).

The employment of an elastic, shape-stable material having moist outside surfaces as coupling members guarantees an acoustically reliable coupling without gas inclusions in the boundary surface. The coupling is reproduceably good, for example, due to the dampness of the outside surface, no disturbing air inclusions occur because of removal and reapplication of the coupling member Such air inclusions can also be easily perceived with the naked eye, given employment of an optical transparent hydro-gel. The coupling is clean, for example, no contamination of the apparatus and of the patient occurs when it is used. As a consequence of the shape stability of the material employed and a consequence of the enclosed insert, the coupling member is easy to manipulate, for example, it is easy to transport, store and to adjust. Hydro-gels are generally not expensive, and their disposal after use is not involved.

The enclosure is preferably a non-metallic fabric or tissue, for example, a material gauze which does not produce any defocussing or other noticeable disruptions during treatment with shock waves. The insert projects somewhat beyond the edge or side and is provided with means for grasping. These means can, for example, comprise the overall projecting part or edge is adequately wide in order to serve as a grasping surface during manipulation. This is preferably true given a cylindrical-polygonal shaping, for example a cuboid or cube shape. Instead, a grasping bracket can also be provided at the projecting part or grasping means.

Another preferred embodiment is characterized in that the coupling member is a coupling medium and preliminary path at the same time.

The coupling member can be fabricated in various thicknesses and can also be adapted to the requirements in therapy. Hydro-gels and other equivalent substances are usually non-toxic and are easily tolerated by the skin. When a clear and transparent material is involved, which is preferred, then the appertaining coupling location can be easily inspected.

During the operation of a shock wave source, for example of a lithotriptor for disintegration of renal calculi, the shock wave pulse is generated with the assistance of an electrical coil, such as disclosed by the above-mentioned copending application and German OS No. 33 28 051, and then checks of the function are appropriate from time to time. These checks, for example, relate to the focus position, the pressure distribution or the pressure amplitude of the shock wave pulse. Such checks are regularly expedient in the use of the shock wave source; however, they are also necessary given initial use after a rebuilding or repair. When, for example, the means focussing the shock wave pulse, such as for example acoustical lens or a reflector is replaced, then a subsequent check must be carried out to see whether a focus position, which is identical to the situation before the replacement, is still present.

A shock wave sensor, which is in particular utilized for lithotripsy is disclosed in German OS No. 34 37 976.

The specific embodiment of the invention under consideration here are based on the consideration that both shock wave sensors, particularly electric manometer elements, as well as shock wave indicators come into consideration as check means for the function check. Given a shock wave indicator, a subsequent evaluation, for example an estimate of the integrally received energy, should be possible in addition to the immediate observation of the point of incidence of the shock wave pulse. The manipulability of the check means is of significance in addition to the manufacturability and the price for the check. A coupling, which is reproducible and loss-free is possible in a defined geometry, is also important.

Another object of the invention is thus to construct a coupling member of the species initially cited which, after the coupling, a simple check of the function of the shock wave source is possible. In particular, it should be possible to monitor the function of the shock wave source during normal operation of the shock wave source, for example, during a lithotripsy treatment.

The solution of this further object is characterized in that the shock wave sensor is contained in the elastic, shape-stable material.

The shock wave sensor, which can be an electric manometer element, but can also be utilized as a shock wave indicator, is preferably embedded in the above-mentioned, shape-stable hydro-gel. All check means suitable for measuring a shock wave fundamentally come into consideration as a shock wave sensor, but particularly small electric manometers and small optical indicators. The coupling members comprising a suitable shape such as, for example, a disk or chunk shape can be put in place on the out-coupling surface of the shock wave source by means of a support mount being put in place therein in a defined relationship to the shock wave source. A good coupling of the shock wave pulse to the shock wave sensor is an advantage. The manipulation in checking the lithotriptor function is essentially comprised of moistening one side of the coupling member, securing the coupling member to the shock wave source and then performing measuring procedure.

The transparent hydro-gel, which is preferably employed, enables a direct observation or even an optical acquisition and evaluation of the front side and/or back side of the shock wave indicator utilized as a sensor without disassembly. If the shock wave sensor utilizes a piezo electric, activated PVDF foil, then indications, which are produced by undesirable movement of the measuring foil, are reduced.

Other advantages and objects will be readily apparent from the following description, the claims and drawings.

BRIEF DESCRIPTION OF THE DRAWINGS

FIG. 6 is a plan view of a cylindrical coupling member in an envelope type of package;

FIG. 7 is a cross-sectional view of a framed coupling member in a pot-shaped packing container;

FIG. 8 is a side view of a shock wave therapy means in accordance with the present invention utilizing a coupling member having a fabric insert such as illustrated in FIG. 5;

FIG. 9 is another type of shock wave means having a coupling member which is held securely by means of clamping forceps;

FIG. 10 is a cross-sectional view of the arrangement of FIG. 9 illustrating the clamping forceps employed therein;

DESCRIPTION OF THE PREFERRED EMBODIMENTS

Figure 1:
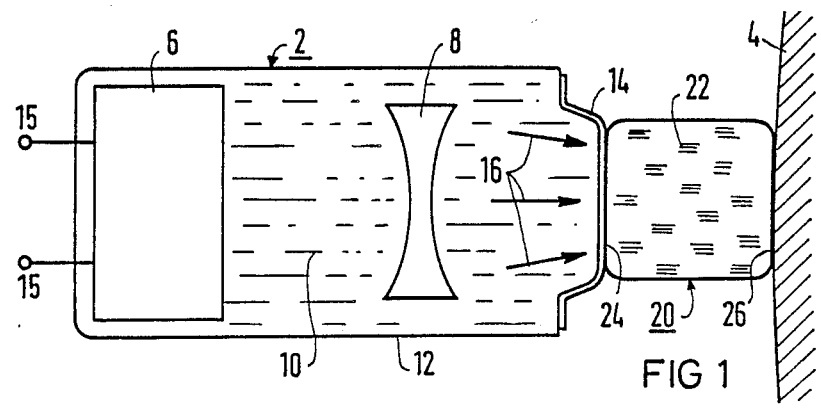
FIG. 1 is a schematic cross-sectional view of a first embodiment of a shock wave therapy device utilizing a coupling member in accordance with the present invention.

The principals of the present invention are particularly useful when incorporated in a shock wave therapy means generally indicated at 2 in FIG. 1. The shock wave therapy means is specifically a disintegration means for concretions such as, for example, renal calculi in a body of a patient 4. The illustrated shock wave means 2 is known per se. It contains a shock wave source 6, a lens 8 and a coupling medium 10, such as, for example, water. The elements 6, 8, and 10 are accommodated in a housing 12 which is terminated at its output side by a membrane 14. The membrane 14 serves as a shock wave emission surface. The shock wave source 6 can be an electro-magnetic means, such as, for example, what is referred to as a shock wave tube, but can also be a piezo ceramic device. The shock wave source has electrical terminals 15. The principal direction of the shock wave focussed by the lens 8 is indicated by arrows 16.

A coupling member 20 is arranged between the exit membrane 14 and the patient 4 to be treated. This coupling member 20 thus serves for the transmission of shock waves on the path between the shock wave source 6 on the one hand of the patient 4 on the other hand. The coupling member 20 is formed of an elastic, shape-stable material 22 which is moist on all sides, for example, has moist outside surfaces 24, 26 and as illustrated has a essentially cylindrical shape.

The material 22 is preferably a material of a hydro-gel, such as a polyacrylamide gel. Such a hydro-gel is viscous, elastic and its front and back moist boundary surfaces 24 or, respectively, 26, easily adapt to the membrane 14 or respectively to the patient 4. This material, thus, is not like a paste, which is easily deformable and soft and which remains adhering both to the membrane 14 as well as to the patient 4 after removal of the coupling member. The matrix of the hydro-gel is water. The impedence and speed of sound of the coupling member 20 can be set by a greater or lesser addition of water during manufacture of the member 20. As shown, the material 22 is rather shape-stable so that it can be fundamentally used without an outside, rigid frame, such is shown later with regard to FIGS. 3 and 4. However, it should be provided with an insert as explained in greater detail with reference to FIGS. such as 5, 6 and 8. The material 22 of the coupling member 20 is cross-linked so that it is essentially homogeneous.

Figure 2:
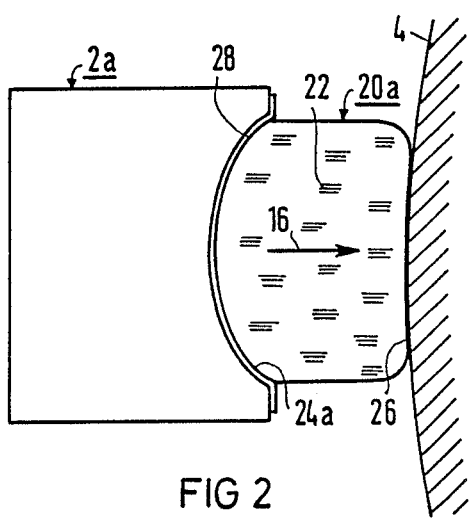
FIG. 2 is a schematic cross-sectional view of a second embodiment of a shock wave therapy means having a concave shock wave exit surface with a coupling member in accordance with the present invention.

In FIG. 2, a different shape and form for the shock wave therapy means or device is indicated at 2a. This shock wave therapy means 2a is equipped with a focussing shock wave source. It can be either a piezo electric member having a calotte-shaped or spherical emission surface or, as shown, can be a shock wave tube having a concave coil and a calotte-shaped emission member in the form of a membrane 28. The latter embodiment of a shock wave tube comprises a concave emission surface is illustrated and is described, for example in German Utility Model No. 84 13 031. A coupling member, generally indicated at 20a, of an elastic, shape-stable material 22 which again has moist outside surfaces 24a and 26 is again mounted between the emission surface 28 and the patient 4. In this embodiment, the coupling member, which is again preferably composed of a hydro-gel, meets two functions, first it serves as a preliminary path, and second, it is used as a coupling medium as a consequence of its moist outside surfaces 24a and 26.

Figures 3, 4, 5:
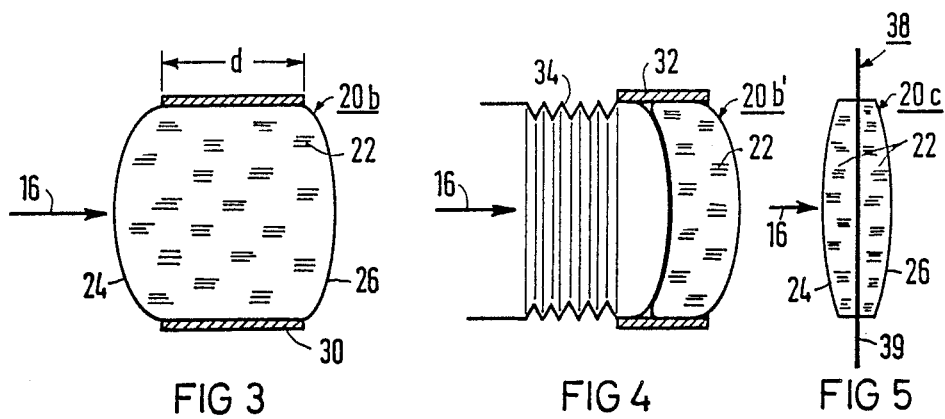
FIG. 3 is a cross-sectional view of a coupling member having a frame or band.
FIG. 4 is a cross-sectional view with portions in elevation for the purpose of illustration with a modification of the same coupling member of FIG. 3 mounted on an end of a shock wave device.
FIG. 5 is a side view of a disc-shaped coupling member having a fabric insert in accordance with the present invention.

An embodiment of the coupling member is generally indicated at 20b in FIG. 3, and essentially is a cylindrical shape which is framed on its edges. A flexible hose piece or band 30, for example, a silicone hose piece, is provided for the frame. This has a width d which is matched to the application and to the coupling member 20b. Various coupling members 20b having different thicknesses can be kept on store for routine examinations. As shown, the two coupling surfaces 24 and 26 at the ends are convexly shaped. Given employment between a shock wave exit surface and patient, they can be deformed to a greater or lesser degree. A hydro-gel is again employed here as the material 22. This is characterized by a low attenuation for the shock waves. The impedence and speed of sound of this medium can be adapted to the body tissue. It should be pointed out as an advantage that both the hose piece 30, as well as the material 22, are transmissive to x-radiation and this enables a locating of the concrement with the coupling member 20b in place.

In a modification of the coupling member is generally indicated at 20b' in FIG. 4 and has a ring 32 for framing the member. The ring 32 is fabricated of a semi-hard material, which is x-ray transmissive. It can be slipped onto the corresponding shaped cooperating member 34 which is connected to the shock wave source (not shown). This cooperating member 34 can, in particular, be a coupling bellows having a known design.

Such a coupling bellows is inflatable in order to set the focus of the disintegration means in a fine regulation or setting. The ring 32 and the material 22 can be kept on hand in various thickness; in this way, a compensation of various thicknesses of the patient examined can be produced. Departing therefrom, only the material 22 fashioned wafer-like can be kept on hand in various thicknesses in order to change it and the ring 32 dependent on the patient thickness.

Another embodiment of the coupling member is indicated at 20c in FIG. 5 and has a shape of a thin disk and is provided with a planar insert 38. This insert 38 is a coarse-weave fabric, such as a gauze, composed of an x-ray permeable material, for example a textile weave. The integration of this fabric serves to increase the mechanical stability and to facilitate the manipulatability of the coupling member 20c. The fabric insert 38 can proceed through the center of the disk and extends perpendicular to the direction of the maximum radiation indicated by the arrow 16. However, there is also applications wherein the embedding of the fabric insert 38 in the proximity of one of the two coupling faces 24 and 26 is more advantageous. As shown in FIG. 5, the insert 38 projects beyond the edges of the elastic, shape-stable material 22 on all sides. It can be grasped on these extended portions and the exposed edges of the insert 38 thus serve as means for increasing the manipulability, for example in an adjustment.

A modification of the coupling member is generally indicated at 20c' in FIG. 6 and shows an interposed insert 38' which is provided with a grasping bracket or projection 40. The overall coupling member 20c' is illustrated as being in a packet 42. This packet or packaging can be a transparent envelope having a rectangular construction which is closed in an air-tight fashion. The envelope can be composed of a plastic bag of, for example, polyethylene which is equipped with a thin metallization. This plastic bag is bonded in an air-tight fashion and thus forms a container. The coupling member 20c' is protected against drying out in this manner. It can be transported and stored over long periods of time in the container or package 42. The coupling member 20c' is not removed from the package 42 until immediately before use. This removal can be facilitated by tear seams 44 and 46 which are provided along two adjacent edges of the package 42.

In FIG. 7, a coupling member 20b' is illustrated as being stored in a pot-like container 50 which is closed air-tight. This container 50 is composed of a small pot 52 having a bent-over peripheral flanged edge to which a transparent foil 54 is bonded. A plastic-coated metal foil can also be used instead of the transparent foil 54. The foil 54 is provided with a rip clip or rip seam 56. The structure of the container 50 is similar to that used for cups of food such as a yogurt cup.

As illustrated in FIG. 8, a gel-like coupling member 20c which has an insert 38 is held fast between the shock wave exit face in the form of the membrane 14 and the patient 4. The projecting edges of the embedded insert 38 serve the purpose of fastening the coupling member 20c to a shock wave source of a shock wave therapy means 2c. This fastening is indicated by two retaining pins 58 and 60 and fastening buttons or clips 62 and 64, respectively, which are engaged therewith. Any other type of fastening can be fundamentally selected.

In FIGS. 9 and 10, the coupling member 20c is illustrated without the insert 38 for purposes of clarity. As illustrated in these figures, two clamping forceps 70 and 72 are provided for securing the coupling member 20c to a shock wave therapy means 2d which has a shock wave source. In certain applications, a single, broad clamping forceps 70 will be sufficient. The second clamping forceps 72 serves the purpose of adapting to different thicknesses of the coupling member 20c.

As illustrated in FIG. 10, the two clamping forceps 70 and 72 are shaped in the fashion of clothespins and they comprise essentially hemispherical clamping legs 82 and 84 which are connected to manipulation legs or handles 88 and 90, respectively, through a rotational axis 86. A spreading spring such as 92 exerts a framing pressure on the coupling member 20c in a clamped condition and lies between the two manipulating legs 88 and 90. For removing the coupling member, the two manipulation legs 88 and 90 merely have to be pressed toward one another.

As clearly illustrated in FIG. 9, the first clamping forceps 70 is secured to a support mount 94 which in turn is attached to the shock wave therapy means 2d.

This support mount 94 can essentially comprise a pipe in which a rod 96 is displaceable in a longitudinal direction. The second clamp forcep 94 is secured to this rod 96. The displaceability in the longitudinal direction is indicated by the double arrow 98. In order to lock the second clamping forcep 92 and the rod 96 in a determined position, a clamping means 100', for example a clamping screw, is provided at the support mount 94. After the adjustment, this prevents a dislocation of the rod 96 in the direction of the double arrow 98 so that the coupling member 20 is effectively fixed in front of the concave emission surface which may be formed by a membrane 28. The coupling member 20c can then easily and quickly be replaced for another coupling member having a different thickness, and this is accomplished by means of releasing the two clamping forceps 70 and 72.

It should be mentioned that the illustrated disintegration means discussed hereinabove can be an ultrasound applicator which is used in the field of ultrasonic diagnosis. Thus, the coupling means, or member, can be utilized with either a device for diagnosis as well as for disintegration.

Figure 11:
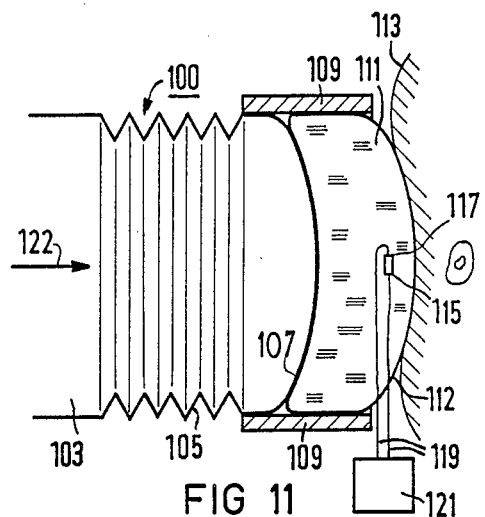
FIG. 11 is a cross-sectional view with portions in elevation of a coupling member including an integrated piezoelectric sensing device.

In FIG. 11, a shock wave source generally indicated at 100 is shown with its essential elements comprising a shock wave generator 103, a preliminary path 105 with a focussing means or arrangement and an out-coupling membrane 107. A coupling member 111 is supported by a hollow-cylindrical mount 109, and is applied to the out-coupling surface or membrane 107. This coupling member 111 is composed of an elastic, shape-stable material particularly of a hydro-gel having moist surfaces. A patient 113 is coupled to the free end face of a coupling surface 112 of the concavo-convex coupling member 111. The coupling member 111 serves for the transmission of shock wave pulses from the shock wave source 103 to the patient 113. This arrangement has already been set forth in detail with reference to FIGS. 1–10.

The coupling member 111 contains a shock wave sensor 115. In the illustrated embodiment, the shock wave sensor 115 is an electrical sensor, specifically a piezo ceramic or piezo crystal 117 which is connected to a measuring instrument 121 via leads 119. The piezo crystal 117 is preferably arranged in a center region of the middle of the coupling member 111, for example on the central axis 122 of the shock wave source 103. It is also possible to provide a plurality of piezo electric crystals next to one another, namely in a radial direction with reference to the central axis 122 or on a ring around the central axis 122.

In normal operations of the shock wave generator 103, for example during lithotripsy treatment of a patient 113, the function of the shock wave source or generator 103 can be continuously checked with the assistance of the piezo crystal 117 and the measuring instrument 121. The check is composed, for example, of monitoring the correct, i.e., prescribed, pressure amplitude of the shock wave pulse at the location of the shock wave sensor 115. By utilizing reference measurements previously undertaken at the work side, it is known that the prescribed amplitude of the shock wave pulse or reference value must occur at the location of the shock wave sensor 115 given proper operation and proper positioning under prescribed operating parameters. For example, an operating voltage of 15 kV, a capacitor capacitance of 0.5 $\mu$F, a preliminary path length of 20 cm, etc. When, during the on-going course of therapy treatment, which can comprise up to 1000 shock wave pulses per patient, the pressure amplitude identified by the shock wave sensor 115 differs from the reference value by a prescribed percentage, then it is evident that there is a possible malfunction of the shock wave generator 103. The identification of the elevated pressure amplitude can then be used in order to interrupt the therapy treatment and too low a pressure amplitude can likewise be a reason for interrupting the therapy treatment and for carrying out a subsequent inspection of the device. Over and above this, the shock wave source 103 can be recalibrated or reset with the shock wave sensor 115 integrated in the coupling member 111 after any repairs or maintenance. When, for example, an electromagnetic flat coil is utilized in a known way as a shock wave generator 103, and this has been replaced by another coil during maintenance, there is the possiblity that the center of the new coil is slightly dislocated. Consequently, the anticipated reference values will not occur given incidence of a shock wave pulse at the shock wave sensor 115 but only a lower value will occur. The coil can be readjusted until the prescribed reference value is obtained. It is then assured that the shock wave means 100 will then have the same property as it had before the maintenance or repair.

The reference value, which is used for readjustment of the shock wave device 100, need not be the same as in what is referred to as an on-line operation with the patient 113. For example, the operating parameters of the voltage value can amount to only 12 kV instead of the said 15 kV in a therapy treatment and can traverse a range from, for example, 12 kV through 20 kV.

Figure 12:
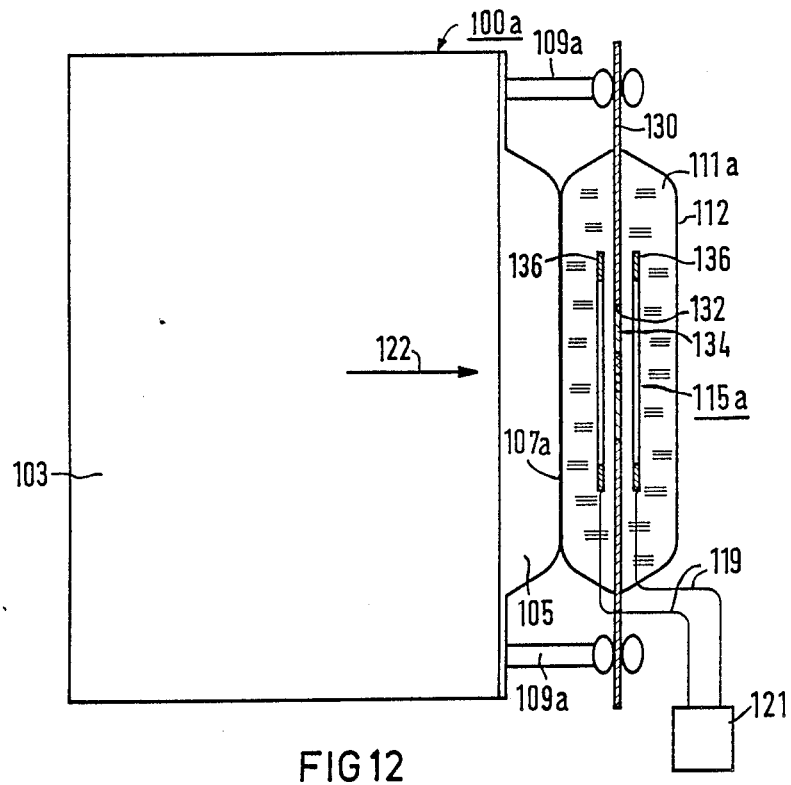
FIG. 12 is a cross-sectional view with portions in elevation of a shock wave source and coupling member comprising an integrated PVDF foil given capacity deviations for measuring signals.

An embodiment of the shock wave device or means is generally indicated at 100a in FIG. 12. The device 100a has a shock wave source or generator 103 with a preliminary path 105, which contains desired focussing means and an out-coupling membrane 107a. A coupling member 111a, which has an embedded metal membrane 130 engages an outer surface of the coupling membrane 107. As illustrated, the membrane 130 has its peripheral edges or portions clamped by externally disposed supports 109a of the device 100a. The metal membrane 130 has a recess or opening 132 at its center which is coaxially relative to the center axis 122 of the shock wave generator 103. The recess 132 is spanned by a partially piezo electric foil, for example a PVDF foil 134, which is piezo electrically activated, for example polarized, in its central region. An annular diverter electrode 136, which is arranged outside of the polarized area is provided at each of the two sides of the PVDF foil 134. The diverter electrodes 136 are connected by lines 119 which lead to a measuring instrument 121. The PVDF foil 134 and the annular diverter electrodes 136 form a shock wave sensor 115a in this embodiment. The shock wave sensor 115a is set forth in detail in German Application P No. 35 45 382.6, which was the basis of U.S. Ser. No. 937,840, Filed Dec. 4, 1986, which issued as U.S. Pat. No. 4,734,611 on Mar. 29, 1988 and whose contents are incorporated by reference thereto.

The shock wave sensor 115a is embedded in a shape-stable, gel-like coupling member 111a, which is held by the perforated metal membrane 130 as mentioned hereinabove. The coupling member 111a is constructed wafer shaped and has its seating surface, which is kept moist lying against the out-coupling membrane 107a in a bubble-free manner. The patient to be treated is coupled to the other surface 112, which is also kept moist.

The incidence of shock wave pulses on the PVDF foil 134 is identified by the capacitative measurement by the measuring instrument 121 through the diverter electrodes 136. Conclusions regarding the amplitude of the shock wave pulse can be obtained from the measured value. Functioning and manipulation of the coupling member 111a are identical to those in accordance with the embodiment of FIG. 11. Here, too, an on-line operation, for example, a continuous monitoring of the shock wave pulses during the therapy treatment, is possible.

Figure 13:
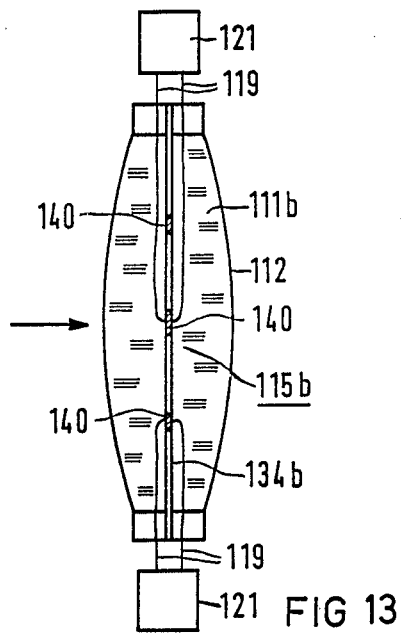
FIG. 13 is a cross-sectional view of a coupling member having integrated PVDF foil given galvanic deviations of the measuring signal.

Another embodiment of the coupling member is illustrated by a coupling member 111b in FIG. 13 and has an integrated shock wave sensor 115b. Here, the shock wave sensor 115b comprises a large area PVDF foil 134b which is provided with recesses on which a respective polarization, for example piezo electric activation is undertaken at prescribed, small sub-areas and on which a metal contact 140 is vapor deposited. The metal contact 140 are respectively connected to a measuring instrument 121 via lines 119. In accordance with this embodiment, the charge, which occurs on the activated sensor face impinged by the shock wave pulse is galvanically detected with the assistance of the metal contacts 140, is galvanically forwarded via the lines 119 and is processed to form a respective measured value in the appertaining measuring instrument 121 which, for example, produces a voltage signal which is the same as the chronological pressure curve. In this embodiment, a plurality of measuring locations lying next to one another or in front of and behind one another as well are simultaneously possibly given employment of a plurality of PFDF foils.

Figure 14:
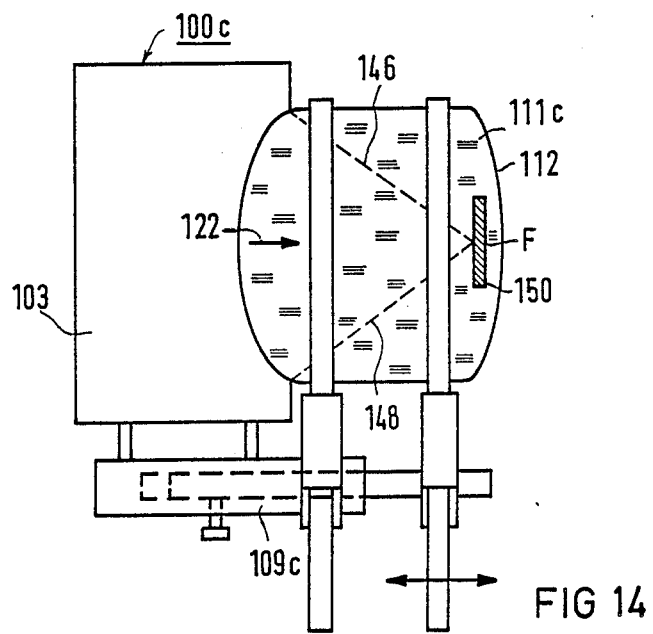
FIG. 14 is a shock wave source and coupling member comprising integrated shock wave indicator.

Another embodiment of a gel-like, shape-stable coupling member 111c is illustrated in FIG. 14 as typically employed during assembly, testing or maintenance jobs. The coupling member 111c is fashioned as a "clump", for example comprises such measurements that the focus F of a shock wave device 100 still lies within the coupling member 111c. This is indicated by the marginal lines 146 and 148. In the present case, the focal plane lies close to the coupling surface 112 at the patient's side. A thin, planar shock wave indicator 150 is introduced into the coupling member 111c at the location of the anticipated focus plane F, for example close to the coupling surface 112. It is also introduced symmetrically relative to a central axis 122. The shock wave indicator 150 is composed, for example, of a round ceramic lamina or plate which experiences a material erosion under the influence of shock waves or is composed of a thin metal foil specifically a lead foil, which deforms or buckles under the influence of shock waves. Electrical connecting lines, thus, are not required in this embodiment. After the assembly, or repair job, the coupling member 111c is positioned in a support mount, such as 109c, with the adjustment values prescribed at the work side for the distance from the shock wave generator 103 for the size of the preliminary path for the distance for the focus means being met. After one or more shock wave pulses have been triggered, the operating personnel can use the shock wave indicator 150, which is positioned in the focal plane F, to see whether a mechanical deformation and/or erosion exists at the desired focal positions. Thus, it is possible to determine if the focus point lies at the prescribed location. In case this is not occurring, further tests and adjustment work can be undertaken.

The shock indicator 150 is preferably provided with a marking which is provided with sectors and circular rings similar to a target used for darts or other types of target practice. Deviations of the focal position can therefore be quantitatively observed and this observation will reduce the cost for the subsequent adjustments.

Although various minor modifications may be suggested by those versed in the art, it should be understood that we wish to embody within the scope of the patent granted hereon all such modifications as reasonably and properly come within the scope of our contribution to the art.

We claim:

1. An essentially homogeneous coupling member for the transmission of shock waves from a chock wave source to a patient to be treated, said coupling member consisting of a member formed of an essentially homogeneous, elastic, shape-stable material having moist outside surfaces, said member including a shock wave sensor being contained in the essentially homogeneous, elastic, shape-stable material of said member.

2. A coupling member according to claim 1, wherein the shock wave sensor comprises a piezo electric PVDF foil.

3. A coupling member according to claim 1, wherein the shock wave sensor comprises a piezo electric device selected from piezo crystals and piezo ceramic elements.

4. A coupling member according to claim 1, wherein the shock wave sensor comprises a thin metal foil which is deformable under the influence of shock waves.

5. A coupling member according to claim 1, wherein the shock wave sensor is a ceramic lamina which is eroded under the influence of the shock waves.

6. A coupling member according to claim 1, wherein the coupling member is fashioned wafer-like and the shock wave sensor is centrally arranged particularly in the middle of the member.

7. A coupling member according to claim 1, wherein the shock wave sensor is arranged adjacent one coupling surface.

8. A coupling member according to claim 1, wherein the member includes an insert having portions extending therefrom to provide grasping means for manipulating and mounting the member.

9. A coupling member according to claim 1, wherein the material of the member is a hydro-gel.

10. A coupling member according to claim 9, wherein the hydro-gel is a polyacrylamide gel.

11. A coupling member for the transmission of shock waves from a shock wave source to a patient, said coupling member being formed by an elastic, shape-stable, essentially homogeneous material having moist outside surfaces, said elastic, shape-stable, essentially homogeneous material having two coupling surfaces, with one of the two coupling surfaces adapted for immediately contacting a shock wave source and another of the two coupling surfaces adapted for immediately contacting a patient, said coupling member including a shock wave sensor being embedded in said elastic, shape-stable, essentially homogeneous material.

* * * * *